United States Patent [19]

Knifton

[11] Patent Number: 5,081,318
[45] Date of Patent: Jan. 14, 1992

[54] ONE STEP SYNTHESIS OF METHYL T-BUTYL ETHER FROM T-BUTANOL USING FLUOROSULFONIC ACID-MODIFIED ZEOLITE CATALYSTS

[75] Inventor: John F. Knifton, Austin, Tex.

[73] Assignee: Texaco Chemical Company, White Plains, N.Y.

[21] Appl. No.: 663,527

[22] Filed: Mar. 4, 1991

[51] Int. Cl.$^5$ .............................................. C07C 41/09
[52] U.S. Cl. ................................. 568/698; 502/64
[58] Field of Search ........................................ 568/698

[56] References Cited

U.S. PATENT DOCUMENTS

| | | | |
|---|---|---|---|
| 3,036,134 | 5/1962 | Matter | 568/698 |
| 3,140,252 | 7/1964 | Frilette et al. | 568/698 |
| 3,175,967 | 3/1965 | Miale et al. | 568/698 |
| 3,553,104 | 12/1967 | Stover et al. | 208/120 |
| 4,822,921 | 4/1989 | Knifton | 568/698 |
| 4,827,048 | 5/1989 | Knifton | 568/698 |

*Primary Examiner*—Howard T. Mars
*Assistant Examiner*—R. Cook
*Attorney, Agent, or Firm*—Jack H. Park; Kenneth R. Priem; Cynthia L. Kendrick

[57] ABSTRACT

A method is disclosed wherein t-butanol is reacted with methanol in a reaction zone in one step to provide methyl tert-butyl ether and the improvement of accomplishing the reaction which comprises:

a. Using a catalyst consisting of a crystalline aluminosilicate faujasite Y-type zeolite which has been treated with a fluorosulfonic acid;

b. continuously contacting said t-butanol and methanol in a molar amount of about 0.1 to 10 moles of methanol per mole of t-butanol with said catalyst at a temperature of about 20° C. to about 250° C. and a pressure of about atmospheric to about 1000 psig to obtain the methyl tert-butyl ether product.

8 Claims, No Drawings

ONE STEP SYNTHESIS OF METHYL T-BUTYL ETHER FROM T-BUTANOL USING FLUOROSULFONIC ACID-MODIFIED ZEOLITE CATALYSTS

CROSS-REFERENCE

This application is related to U.S. Pat. Nos. 4,827,048 and 4,822,921 and to application Ser. Nos. 07/494,280 and 07/494,281.

This invention concerns an improved process for preparing methyl tertiary-butyl ether (MTBE) by the reaction of tertiary butanol and methanol in the presence of a catalyst comprising a fluorosulfonic acid-modified Y-zeolite. The invention is particularly advantageous in that the reaction takes place in one-step, the catalyst exhibits total MTBE plus isobutylene selectivity close to 100% and levels of tert-butanol conversion as high as 86% are achieved with the crude product mix separating into an isobutylene-MTBE product-rich phase and a heavier aqueous methanol phase.

BACKGROUND OF THE INVENTION

It is known to those skilled in the art that ethers, including unsymmetrical ethers, may be prepared by reacting an alcohol with another alcohol to form the desired product. The reaction mixture, containing catalyst and/or condensing agent may be separated and further treated to permit attainment of the desired product. Such further treatment commonly includes one or more distillation operations.

Methyl tert-butyl ether is finding increasing use as a blending component in high octane gasoline as the current gasoline additives based on lead and manganese are phased out. Currently all commercial processes for the manufacture of methyl tert-butyl ether are based upon the liquid-phase reaction of isobutylene and methanol (Eq. 1), catalyzed by a cationic ion-exchange resin (see, for example: Hydrocarbon Processing, Oct. 1984, p. 63; Oil and Gas J., Jan. 1, 1979, p. 76; Chem. Economics Handbook-SRI, Sept. 1986, p. 543–7051P). The cationic ion-exchange resins used in MTBE synthesis normally have the sulphonic acid functionality (see: J. Tejero, J. Mol. Catal., 42 (1987) 257; C. Subramamam et al., Can. J. Chem. Eng., 65 (1987) 613).

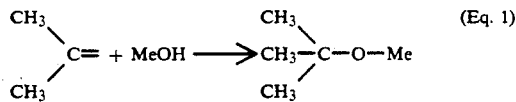

(Eq. 1)

With the expanding use of MTBE as an acceptable gasoline additive, a growing problem is the availability of raw materials. Historically, the critical raw material is isobutylene (Oil and Gas J., June 8, 1987, p. 55). It would be advantageous, therefore, to have a process to make MTBE that does not require isobutylene as a building block. It would be advantageous to have an efficient process for making MTBE by reaction of methanol with tertiary butyl alcohol, since t-butanol (TBA) is readily available commercially through isobutane oxidation.

In U.S. Pat. No. 4,144,138 (1979) to Rao et al., there is disclosed a method for recovering methyl tertiary butyl ether from etherification reaction effluent by azeotropic distillation to recover methanol-ether azeotrope overhead which is water-washed to give pure ether raffinate, the latter being azeotropically distilled to yield ether-methanol overhead which is recycled to water washing.

The preparation of methyl tert-butyl ether from methyl and tert-butyl alcohols is discussed in S. V. Rozhkov et al., Prevrashch Uglevodorodov, Kislotno-Osnovn. Geterogennykh Katal. Tezisy Dokl. Vses Konf., 1977, 150 (C. A. 92:58165y). Here the TBA and methanol undergo etherification over KU-2 strongly acidic sulfopolystyrene cation-exchangers under mild conditions. This reference contains data on basic parameters of such a process. It is also pointed out that, although a plant for etherification over cation exchangers does not present any major problems, considerations include the fact that recycling large amounts of tert-butyl alcohol and methanol, as well as isobutylene, causes the scheme to be somewhat more expensive. Also, the progress of the reaction over cation exchangers is usually complicated by various adsorption and diffusion factors, by swelling phenomena, and by the variable distribution of the components between the solution and ion-exchanger phase. Furthermore, said acidic cation-exchangers with an organic (polystyrene or polymethacrylate) backbone generally have a very limited stability range with regard to operating temperatures, with temperatures above 120° C. normally leading to irreversible destruction of the resin and loss of catalytic activity.

In U.S. Pat. No. 2,282,469 to Frolich there is disclosed a process for preparing methyl tertiary butyl ether over a catalyst comprising Kieselguhr impregnated with phosphoric acid at a temperature of about 175° F. to 350° F.

Japanese Patent 0007432 teaches the use of zeolites to make dialkyl ethers containing primary or secondary alkyl groups. The zeolites have a porous structure and are represented by:

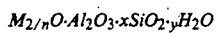

where M is an alkali metal or alkaline earth metal cation or organic base cation, n is the valence of the cation and x and y are variables.

U.S. Pat. No. 4,058,576 to Chang et al. teaches the use of (pentasil-type) aluminosilicate zeolites, such as ZSM-5, having a pore size greater than 5 angstrom units and a silica-to-alumina ratio of at least 12, to convert lower alcohols to a mixture of ethers and olefins.

In U.S. Pat. No. 4,822,921 there is disclosed a method for producing MTBE by reacting tertiary butyl alcohol and methanol in the presence of a catalyst comprising an inert support, such as titania, having a phosphoric acid impregnated thereon.

U.S. Pat. No. 4,827,048 discloses a method for producing MTBE by reacting tertiary butyl alcohol and methanol in the presence of a catalyst comprising a heteropoly acid such as 12-tungstophosphoric acid or 12-molybdophosphoric acid on an inert support, such as titania.

In copending U.S. patent application Ser. No. 07/494,281, there is disclosed a method for preparing methyl tertiary butyl ether by reacting butanol and methanol in the presence of a catalyst comprising a super-acid alumina or a faujasite-type zeolite.

Copending U.S. patent application Ser. No. 07/494,280 discloses the reaction of butanol and methanol in the presence of acidic montmorillonite clay catalysts having certain identifiable physical parameters.

It would be a substantial advance in the art if methyl tertiary butyl ether could be selectively synthesized from tertiary butyl alcohol and methanol in one step using a catalyst which allows for rapid conversion of t-butanol. It has now been discovered that fluorosulfonic acid modified Y-zeolites can be used as catalysts for the selective synthesis of methyl tertiary butyl ether from tertiary butyl alcohol and methanol. The accompanying examples demonstrate a significant improvement in yield of MTBE when using the modified Y-type zeolites of the instant invention for such a reaction.

SUMMARY OF THE INVENTION

In accordance with certain of its aspects, the novel method of this invention for preparing methyl tert-butyl ether from tertiary butyl alcohol (t-butanol) and methanol in one-step comprises reacting tertiary butyl alcohol and methanol in the presence of a catalyst comprising an acid-modified zeolite at an elevated temperature and moderate pressure. Examples demonstrate particularly the effectiveness of triflic acid-modified Y-zeolites.

DESCRIPTION OF THE INVENTION

Preparation of the product of this invention may be carried out typically by reacting tertiary butyl alcohol and methanol in the presence of an etherification catalyst. The etherification is carried out in one step and the catalyst preferably comprises a rare earth exchanged Y-zeolite modified with a fluorosulfonic acid.

The reaction can be represented by the following:

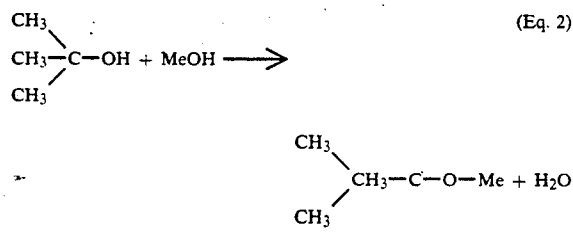

(Eq. 2)

Generally the methanol and t-butanol coreactants may be mixed in any proportion in order to generate the desired methyl t-butyl ether, but preferably the molar ratio of methanol to t-butanol in the feed mixture should be between 10:1 and 1:10, if the yield of desired MTBE is to be maximized. In order to achieve maximum selectivity to MTBE, and optimum conversion per pass, an excess of methanol in the liquid feed is desirable. The most preferred methanol-to-tertiary butanol molar ratio is from 1:1 to 5:1.

In certain circumstances, it may be particularly desirable that the TBA conversion be high enough (e.g. >80% per pass), such that the crude product mix phase separates into an isobutylene-MTBE product-rich phase and a heavier aqueous methanol phase. Preferably such a product phase separation would be achieved at as low an etherification temperature as possibly, but particularly in the range 160°–200° C.

The same process may also be applied to the preparation of other alkyl tertiary alkyl ethers. For example, said process may be applied to the reaction of a $C_1$–$C_6$ primary alcohol such as methanol, ethanol, n-propanol and n-hexanol with a $C_4$–$C_{10}$ tertiary alcohol such as, for example, tertiary butanol and tertiary amyl alcohol. Reaction of methanol with tertiary amyl alcohol (2-methyl-2-butanol) would then yield methyl tertiary amyl ether (TAME). Alternatively a mixture of alcohols, e.g., a mixture of $C_1$–$C_5$ alcohols, could be reacted to give a mixture of alkyl tert-alkyl ethers.

Good results were realized using certain crystalline aluminosilicate zeolites as catalysts for Reaction 2, particularly the isostructural group of faujasite zeolites that include the synthetic Y-zeolites. The preferred Y-zeolites are the rare earth exchanged Y-zeolites.

The unit cells of zeolites are cubic, $a_o \approx 2.5$ nm, and each contains 192 silicon- or aluminum-centered oxygen tetrahedra which are linked through shared oxygen atoms. Because of the net negative charge on each of the aluminum-centered tetrahedra, each unit cell contains an equivalent number of charge-balancing cations. These are exclusively sodium ions in zeolites in their synthesized form. Typical cell contents for the Y-zeolites in the hydrated form are:

$$Na_{56}[(AlO_2)_{56}(SiO_2)_{136}] \cdot 250 \, H_2O$$

Y-zeolites are distinguished on the basis of the relative concentration of silicon and aluminum atoms and the consequent effects on detailed structure and related chemical and physical properties. The aluminum atoms in the unit cell of Y-zeolite vary from 76 to 48 giving a Si:Al ration between 1.5 and 3.0. Both the cation concentration and charge density on the aluminosilicate structure are lower for Y-zeolites than for X-zeolites, where the aluminum atoms in the unit cell vary from 96 to 77.

The feature which determines the difference between faujasites and other zeolites built up from sodalite units is the double 6-membered ring or hexagonal prism, by which the units are linked. The sodalite unit, or $\beta$-cage, can be represented by a truncated octahedron, with the 24 silicon or aluminum atoms (designated T atoms) taking positions at the vertices. The 36 oxygen atoms are displaced from the midpoints of the edges joining the vertices in order to attain tetrahedral configuration around the T atoms. The free diameter of the void within the $\beta$-cage is 0.66 nm, but only the smallest molecules can enter through the 0.22 nm diameter opening in the distorted ring of six oxygen atoms associated with each hexagonal face. Each sodalite unit is linked tetrahedrally across hexagonal faces by six bridging oxygens to four other sodalite units. The larger void spaces enclosed by sodalite units and hexagonal prisms are termed $\alpha$-cages, or supercages. The $\alpha$-cage is a 26-hedron with a free diameter of $\approx 1.3$ nm, and it can be entered through four distorted 12-member rings of diameter 0.80–0.90 nm. In this way each $\alpha$-cage is tetrahedrally joined to four others giving a complex system of void space extending throughout the zeolite structure. The $\alpha$- and $\beta$-cages together give Y-zeolites, along with X-zeolites, the largest void volume of any known zeolites, which is ca. 50 vol% of the dehydrated crystal. From the catalytic viewpoint, the $\alpha$-cages are by far the most important, since, unlike the $\beta$-cages, they permit entry of numerous aliphatic and aromatic compounds.

Particularly effective in the subject synthesis of MTBE are the synthetic Y-zeolites. Preferably said zeolites should be in a strongly acidic form whereby some, or all, of the cations (Group I or II, alkali or alkaline earth metal ions such as sodium, potassium, calcium or magnesium) are exchanged by protons either through ammonium exchange followed by thermal stabilization (deammoniation, removal of $NH_3$) at elevated temperatures (e.g. 400°–500° C.) through mineral acid treatment, etc. Alternatively, said Y-zeolites may be dealuminized by hydrothermal treatment, by mineral acid treatment or by treatment with ethylenediaminetetraacetic acid (EDTA) or other chelating agents, in which case said dealuminized Y-zeolites should have a Si:Al ratio of greater than three. A further possibility is that said Y-zeolites may be rare-earth exchanged with, for example, a mixture of rare-earth salts, by treatment with lanthanum salts, etc. Said rare-earth exchanged Y-zeolites would then have a Si:Al ratio of 1.5 to 3. The exchange of the sodium ions of the Y-zeolite by rare earth ions has been reviewed (see, for example, R. Rudham and A. Stockwell, The Chemical Society Specialist Periodical Report - Catalysis, Vol I, 1977, Chapter 3).

The acid useful for modifying the Y-type zeolite is an acid from the group consisting of fluorosulfonic acid and its congeners. These fluorosulfonic acids can be substituted with an alkyl group as in the case of trifluoromethanesulfonic acid (triflic acid). Example 2 demonstrates the effectiveness of triflic acid.

The performance of such zeolites in MTBE synthesis from t-butanol and methanol in one-step (Eq. 2) is illustrated by the accompanying examples.

Said catalysts may be in the form of powders, pellets, granules, spheres, shapes and extrudates. The examples described herein demonstrate the advantages of using extrudates. Illustrative of suitable zeolites which can be modified with fluorosulfonic acid or trifluoromethane sulfonic acid for the one-step synthesis of MTBE from methanol plus t-butanol include typical Y-type zeolites, particularly the rare-earth exchanged zeolites such as the Linde SK-500 extrudates, having a Si:Al ratio of between 1.5:1 and 2:1. As will be demonstrated by the examples, these catalysts are preferably of high purity and high surface area (i.e. >100 m²/g).

The reaction may be carried out in either a stirred slurry reactor or in a fixed bed continuous flow reactor. The catalyst concentration should be sufficient to provide the desired catalytic effect.

Etherification can generally be conducted at temperatures from 20° to 250° C.; the preferred range is 80° to 200° C. The total operating pressure may be from 0 to 1000 psig, or higher. The preferred pressure range is 50 to 500 psig.

Typically, MTBE is generated continuously in up to ca. 40 wt % concentration in the crude liquid product at total liquid hourly space velocities (LHSV) of up to 6 or higher and relatively mild conditions, where:

$$LHSV = \frac{\text{Volume Total Liquid Feed Run Through The Reactor Per Hour}}{\text{Volume of Catalyst In Reactor}}$$

The examples which follow illustrate the one-step synthesis of MTBE from TBA and MeOH (Eq. 2) using Y-type zeolites particularly the form of high surface area powders. The examples are only intended as a means of illustration and it is understood the invention is not meant to be limited thereby.

Conversions of t-butanol (TBA, wt %) are estimated in the following examples using the equation:

$$\frac{\text{(Wt \% Conc. of TBA in Feed} - \text{Wt \% Conc. of TBA in Product)}}{\text{Wt \% Conc. of TBA in Feed}} \times 100$$

Selectivities of methyl t-butyl ether (MTBE, mole %) and isobutylene ($C_4H_8$, mole%) are estimated from:

$$\frac{\text{Moles of MTBE (or } C_4H_8 \text{) in Product}}{\text{moles of TBA converted}} \times 100$$

It may be noted that:

a) In Example 2, using the triflic acid-modified zeolite-Y of Example 1 and a low MeOH/TBA molar feed ratio of 1:1:1, typically the t-butanol (TBA) conversion per pass is 70% and 86% at 140° and 160° C. operating temperatures, respectively. By contrast, in comparative Example B, using the unmodified Y-zeolite, at the same 140° and 160° C. operating temperatures, the TBA conversions are only 56% and 78% respectively.

b) In Example 2, using the triflic acid-modified Y-zeolite of Example 1, desirable product phase separation into an isobutylene plus MTBE product-rich phase and a heavier aqueous methanol-rich phase is achieved at 160° C. (see Table 1) whereas with the unmodified Y-zeolite, this same desirable phase separation requires an operating temperature of 180° C. (see Table 5).

c) In Examples 3 and 4, the triflic acid-modified Y-zeolite provided good performance over 21 days at both 160° and 120° C. operating temperatures (see Tables 2 and 3), whereas in the comparative Example A the unmodified zeolite-Y gave both lower initial TBA conversions and a serious decline in activity over the same 21 day period (see Table 4).

EXAMPLE 1

This example illustrates the preparation of the triflic acid modified Y-zeolite.

To 200 g of Y-zeolite (Linde SK-500, Si:Al ratio ca. 1.5→2:1, 1/16" diameter extrudates, dried at 175° C. for 3 hours in vacuo) is added a solution of trifluoromethanesulfonic acid (20 g) in dried acetone (400 cc, dried over 4A sieve). The mixture was stirred for 3-4 hours, filtered and the solids washed with distilled water and dried in vacuo at 40° C., overnight and at 150° C. for 4 hours.

The recovered light brown extrudates were found to contain by analysis:
$SO_4^{2-}$, 0.57%
$H_2O$, 0.93%
Acidity, 0.13 meq/g

EXAMPLE 2

This example illustrates the production of methyl t-butyl ether from t-butanol and methanol using a triflic acid-modified Y-zeolite.

Synthesis was conducted in a tubular reactor (0.56" id, 12" long), constructed of 316 stainless steel, operated upflow and mounted in a furnace controllable to ±1.0° C. and fitted with pumps allowing flow control to <±1 cc/hr. The reactor was also fitted with a pressure regulating device and equipment for monitoring temperature, pressure and flow rate.

The reactor was charged at the beginning of the experiment with 25 cc triflic acid Y-zeolite extrudates prepared by the method of Example 1 A screen of glass wool was placed at the top and bottom of the reactor to ensure the catalyst would remain in the middle portion.

The catalyst bed was treated with a methanol/t-butanol 10 (1.1:1 molar mix) upflow, at a flow rate of 50 cc/hr (LHSV 2), while the reactor was held at 100° C., with a total pressure of 300 psi. Samples of crude product effluent were collected periodically on-stream, in 316 ss bombs, and analyzed by glc and gc-ir.

Typical analyses data for samples taken under these conditions are summarized in Table 1. Performance at a series of other temperature (120°, 140°, 160°, 180° C.) and flow rate (160 cc/hr, LHSV 6.4) was determined using the same procedure. These results are also given in Table 1. Of note, t-butanol conversion levels at 140° and 160° C. and isobutylene/MTBE selectivities at 140° C. are as follows:

| Sample | Operating Temp (°C.) | TBA Conv. (%) | Molar Selectivity (%) | |
|---|---|---|---|---|
| | | | $C_4H_8$ | MTBE |
| 5 | 140 | 70 | 34 | 66 |
| 7 | 160 | 86 | — | — |

EXAMPLE 3

This Example illustrates the performance of the triflic acid-modified zeolite-Y in the production of methyl t-butyl ether from t-butanol and methanol over an extended period.

Using the equipment and procedures of Example 2, 25 cc of the triflic acid-modified zeolite-Y (prepared as described in Example 1) was charged to the reactor system and performance was monitored over 21 days at an operating temperature of 160° C. The TBA/MeOH (1:1.1) feed rate was maintained at 50 cc/hr. The results are summarized in Table 2.

Calculated TBA conversion and $C_4H_8$/MTBE selectivities for typical samples are as follows:

| Sample | Time On Stream Days | TBA Conv. (%) | Molar Selectivity (%) | |
|---|---|---|---|---|
| | | | $C_4H_8$ | MTBE |
| 1 | 1 | 81 | 40 | 57 |
| 8 | 21 | 76 | 41 | 56 |

EXAMPLE 4

This Example illustrates the performance of the triflic acid-modified zeolite-Y in the production of methyl t-butyl ether from t-butanol and methanol over an extended period.

Using the equipment and procedures of Example 2, 25 cc of the triflic acid-modified zeolite-Y (prepared as described in Example 1) was charged to the reactor system and performance was monitored over 21 days at an operating temperature of 120° C. The TBA/MeOH (1:1.1) feed rate was maintained at 50 cc/hr. The results are summarized in Table 3.

Calculated TBA conversion and $C_4H_8$/MTBE selectivities for typical samples are as follows:

| Sample | Time On Stream Days | TBA Conv. (%) | Molar Selectivity (%) | |
|---|---|---|---|---|
| | | | $C_4H_8$ | MTBE |
| 1 | 1 | 58 | 26 | 74 |
| 7 | 21 | 54 | 26 | 71 |

COMPARATIVE EXAMPLES A

This comparative example illustrates the performance of unmodified zeolite-Y in the production of methyl t-butyl ether from t-butanol and methanol.

Using the equipment and procedures of Example 2, 25 cc of Y-zeolite (Linde SK-500, 1/16" diameter extrudates) was charged to the reactor system and performance was monitored over 21 days at an operating temperature of 160° C. The TBA/MeOH (1:1.1) feed rate was maintained at 50 cc/hr. The results are summarized in Table 4.

Calculated TBA conversions and $C_4H_8$/MTBE selectivities for Samples 3 and 9 are as follows:

| Sample | Time On Stream Days | TBA Conv. (%) | Molar Selectivity (%) | |
|---|---|---|---|---|
| | | | $C_4H_8$ | MTBE |
| 3 | 6 | 74 | 59 | 42 |
| 9 | 21 | 58 | 49 | 53 |

COMPARATIVE EXAMPLE B

This comparative example illustrates the performance of unmodified zeolite-Y in the production of methyl t-butyl ether from t-butanol and methanol over a range of conditions.

Using the equipment and procedures of Example 2, 25 cc of Y-zeolite (Linde SK-500, 1/16" diam. extrudates) was charged to the reactor system and performance was monitored over a range of operating temperatures (100°–180° C.) and flow rates (50–160 cc/hr, LHSV 2–6.4). The results are summarized in Table 5.

Calculated TBA conversion and $C_4H_8$/MTBE selectivities at 140° and 160° C. are typically as follows:

| Sample | Time On Stream Days | TBA Conv. (%) | Molar Selectivity (%) | |
|---|---|---|---|---|
| | | | $C_4H_8$ | MTBE |
| 6 | 140 | 56 | 35 | 64 |
| 8 | 160 | 78 | 59 | 39 |

TABLE 1

| Ex. | Catalyst | MeOH/TBA Molar Ratio | Temp. (°C.) | Feed Rate (cc/hr) | Time On Stream (Days) | SAMPLE | PRODUCT COMPOSITION (WT %) | | | | |
|---|---|---|---|---|---|---|---|---|---|---|---|
| | | | | | | | $H_2O$ | MeOH | $C_4H_8$ | TBA | MTBE |
| 2 | Ex. 1[a] | | | | | Feed Sample | | 30.4 | | 69.2 | |
| | | 1.1:1 | 100 | 50 | 1 | 1 | 4.4 | 24.9 | 4.3 | 48.5 | 17.8 |
| | | | | | | 2 | 5.4 | 23.6 | 5.2 | 44.5 | 21.2 |
| | | | 120 | 50 | 2 | 3 | 8.8 | 18.7 | 8.3 | 29.1 | 35.1 |
| | | | | | | 4 | 9.0 | 18.7 | 8.1 | 29.5 | 34.5 |
| | | | 140 | 50 | 3 | 5 | 10.9 | 17.6 | 12.6 | 20.9 | 37.8 |
| | | | | | | 6 | 11.6 | 17.5 | 12.5 | 21.0 | 37.3 |
| | | | 160 | 50 | 4 | 7 | 5.0 | 15.60 | 39.4 | 9.1 | 30.6[b] |
| | | | | | | | 34.2 | 40.7 | 4.6 | 9.7 | 10.4[b] |
| | | | | | | 8 | 5.0 | 16.1 | 38.7 | 10.1 | 29.9[b] |

TABLE 1-continued

| Ex. | Catalyst | MeOH/TBA Molar Ratio | Temp. (°C.) | Feed Rate (cc/hr) | Time On Stream (Days) | SAMPLE | PRODUCT COMPOSITION (WT %) | | | | |
|---|---|---|---|---|---|---|---|---|---|---|---|
| | | | | | | | H$_2$O | MeOH | C$_4$H$_8$ | TBA | MTBE |
| | | | 180 | 50 | 5 | 9 | 35.1 | 39.9 | 4.6 | 9.8 | 10.3[b] |
| | | | | | | | 16.4 | 35.0 | 12.1 | 6.9 | 29.6[b] |
| | | | | | | | 28.1 | 46.5 | 4.3 | 8.7 | 12.3[b] |
| | | | | | | 10 | 12.7 | 26.4 | 19.3 | 6.8 | 34.8[b] |
| | | | | | | | 27.9 | 44.9 | 6.4 | 7.8 | 12.9[b] |
| | | | 160 | 160 | 6 | 11 | 9.1 | 22.1 | 11.1 | 31.9 | 25.4 |
| | | | | | | 12 | 9.3 | 22.0 | 12.9 | 29.9 | 25.8 |

[a]Triflic acid (CF$_3$SO$_3$H)-on-SK-500.
[b]Product two layers.

TABLE 2

| Ex. | Time On Stream (Days) | Sample | PRODUCT COMPOSITION (WT %) | | | | |
|---|---|---|---|---|---|---|---|
| | | | H$_2$O | MeOH | C$_4$H$_8$ | TBA | MTBE |
| 3 | | Feed Samples | | 31.3 | | 68.5 | |
| | 1 | 1 | 12.6 | 21.3 | 17.0 | 13.0 | 36.1 |
| | 12 | 5 | 10.2 | 22.3 | 16.1 | 15.2 | 35.7 |
| | 21 | 8 | 10.8 | 22.0 | 16.2 | 16.5 | 34.5 |

TABLE 3

| Ex. | Time On Stream (Days) | Sample | PRODUCT COMPOSITION (WT %) | | | | |
|---|---|---|---|---|---|---|---|
| | | | H$_2$O | MeOH | C$_4$H$_8$ | TBA | MTBE |
| 4 | | FS | | 31.9 | | 67.6 | |
| | 1 | 1 | 9.4 | 19.6 | 7.6 | 28.5 | 34.5 |
| | 11 | 4 | 8.1 | 18.5 | 8.1 | 31.0 | 34.0 |
| | 21 | 7 | 8.6 | 20.8 | 7.4 | 31.6 | 31.3 |

TABLE 4

| Ex. | Time On Stream (Days) | Sample | PRODUCT COMPOSITION (WT %) | | | | |
|---|---|---|---|---|---|---|---|
| | | | H$_2$O | MeOH | C$_4$H$_8$ | TBA | MTBE |
| A | | FS | | 29.6 | | 70.00 | |
| | 6 | 3 | 11.3 | 21.4 | 22.8 | 18.5 | 25.9 |
| | 12 | 6 | 9.7 | 21.0 | 17.0 | 25.0 | 27.2 |
| | 21 | 9 | 8.5 | 21.8 | 14.8 | 29.7 | 25.2 |

TABLE 5

| Ex. | Catalyst | MeOH/TBA Molar Ratio | Temp. (°C.) | Feed Rate (cc/hr) | Time On Stream (Days) | SAMPLE | PRODUCT COMPOSITION (WT %) | | | | |
|---|---|---|---|---|---|---|---|---|---|---|---|
| | | | | | | | H$_2$O | MeOH | C$_4$H$_8$ | TBA | MTBE |
| B | SK-500 | | | | | FS | | 31.4 | | 68.2 | |
| | | 1.1:1 | 100 | 50 | 1 | 1 | 4.2 | 25.2 | 4.5 | 49.3 | 16.6 |
| | | | | | | 2 | 3.6 | 25.3 | 4.1 | 51.0 | 15.9 |
| | | | 120 | 50 | 2 | 3 | 8.3 | 21.5 | 6.9 | 36.3 | 26.9 |
| | | | | | | 4 | 8.6 | 21.0 | 7.7 | 34.0 | 28.7 |
| | | | 140 | 50 | 3 | 5 | 11.0 | 17.6 | 10.0 | 26.7 | 34.6 |
| | | | | | | →6 | 11.3 | 19.0 | 11.8 | 23.5 | 34.3 |
| | | | 160 | 50 | 4 | 7 | 12.9 | 21.4 | 24.7 | 15.2 | 25.5 |
| | | | | | | →8 | 13.5 | 22.2 | 24.0 | 14.9 | 25.1 |
| | | | 180 | 50 | 5 | 9 | 14.1 | 31.6 | 10.4 | 8.8 | 35.1[a] |
| | | | | | | | 31.8 | 41.4 | 7.1 | 7.5 | 11.5 |
| | | | | | | 10 | 17.0 | 31.7 | 17.0 | 7.3 | 27.2[a] |
| | | | | | | | 30.0 | 38.8 | 8.0 | 8.6 | 14.1 |
| | | | 160 | 160 | 6 | 11 | 10.1 | 22.2 | 13.1 | 29.7 | 24.9 |
| | | | | | | 12 | 9.8 | 22.1 | 13.1 | 29.9 | 25.0 |

[a]Product two phases.

What is claimed is:

1. In a method wherein t-butanol is reacted with methanol in a one step in the presence of a catalyst to provide methyl tert-butyl ether, the improvement of using as a catalyst a crystalline aluminosilicate faujasite-type Y-zeolite modified with a fluorosulfonic acid and continuously contacting said t-butanol and methanol in a molar amount of about 0.1 to 10 moles of methanol per mole of t-butanol with said catalyst at a temperature of about 20° C. to about 250° C. and a pressure of about atmospheric to about 1000 psig to obtain methyl tert-butyl ether product.

2. The method of claim 1 wherein the fluorosulfonic acid is selected from the group consisting of fluorosulfonic acid and trifluoromethanesulfonic acid.

3. The method of claim 1 wherein the fluorosulfonic acid is trifluoromethane sulfonic acid.

4. The method of claim 1 wherein the Y-zeolite is rare-earth exchanged.

5. The method of claim 1 wherein said rare-earth exchanged Y-zeolite has a Si to Al ratio of 1.5 to 3.

6. The method of claim 1 wherein the Y-zeolite catalyst has a surface of greater than 100 m$^2$/g.

7. The method of claim 1 wherein the temperature is from about 80° C. to about 200° C.

8. The method of claim 1 wherein the operating temperature is in the range 160° to 200° C. and the product comprises a two-phase mix of an isobutylene-methyltertiarybutyl ether product-rich phase and a heavier aqueous methanol-rich phase.

* * * * *